United States Patent [19]

Ruiz-Razura et al.

[11] Patent Number: 5,083,576
[45] Date of Patent: Jan. 28, 1992

[54] ELONGATION OF LINEAR AND TUBULAR TISSUE

[75] Inventors: Amado Ruiz-Razura; Benjamin E. Cohen, both of Houston, Tex.

[73] Assignee: Inamed Development Company, Carpinteria, Calif.

[21] Appl. No.: 503,429

[22] Filed: Apr. 2, 1990

Related U.S. Application Data

[63] Continuation-in-part of Ser. No. 488,455, Feb. 26, 1990, abandoned, which is a continuation of Ser. No. 340,431, Apr. 19, 1989, abandoned.

[51] Int. Cl.⁵ .................... A61B 19/00; A61B 17/00
[52] U.S. Cl. ......................... 128/898; 604/96; 623/8
[58] Field of Search ............... 623/8; 604/96, 103, 604/104; 128/898

[56] References Cited

U.S. PATENT DOCUMENTS

| | | | |
|---|---|---|---|
| 4,666,447 | 5/1987 | Smith et al. | 623/8 |
| 4,685,447 | 8/1987 | Iversen et al. | 623/8 |
| 4,738,657 | 4/1988 | Hancock et al. | 623/8 |
| 4,823,815 | 4/1989 | Watson et al. | 623/8 |
| 4,841,992 | 6/1989 | Sasaki et al. | 623/8 |
| 4,863,469 | 9/1989 | VanBeek et al. | 623/8 |

Primary Examiner—Stephen C. Pellegrino
Assistant Examiner—Gary Jackson
Attorney, Agent, or Firm—Michael G. Petit

[57] ABSTRACT

An inflatable envelope and a procedure for using it for the purpose of elongating tubular or linear tissue during the acute phase of a surgical procedure. The envelope has a path upon which the tissue is aligned, whose path length increases with inflation of the envelope. Successive inflations and deflations result in elongation of the tissue enabling re-connection of ends of the tissue which before were significantly spaced apart.

6 Claims, 2 Drawing Sheets

ELONGATION OF LINEAR AND TUBULAR TISSUE

CROSS REFERENCE TO OTHER APPLICATIONS

This application is a continuation-in-part of applicants presently co-pending U.S. patent application Ser. No. 07/488,455, filed Feb. 26, 1990, now abandoned, entitled "Elongation Of Blood Vessels", which is in turn a file wrapper continuation of applicants' then co-pending patent application Ser. No. 07/340,431 filed Apr. 19, 1989, now abandoned, entitled "Elongation of Blood Vessels".

FIELD OF THE INVENTION

This invention relates to elongation of linear and tubular tissue, for example blood vessels (tubular tissue) and nerves (linear tissue), in order that a defective protion can be removed, and the remaining ends of the tissues may be directly rejoined without interposition of a section of another vessel or connective device, to provide connection for the tissue.

BACKGROUND OF THE INVENTION

This invention relates to the elongation of certain types of tissue, namely linear and tubular tissue. Such tissue constitutes many important parts of the human anatomy, which parts sometimes become diseased or severed. Restoration of function requires removal of diseased or damaged tissue, and reconnection of the severed ends.

The problem with the reconnection is that there often is insufficient remaining length of the tissue to enable a direct reconnection, and parts of other similar tissue, or artificial implants such as synthetic plastic tubing must be provided. Such procedures can be very time consuming, especially when tissue must be harvested from some other part of the anatomy, and then emplaced.

It is an object of this invention to enable tissue to be elongated on an acute basis, during the operative repair procedure, whereby to obviate the need for harvesting other tissue. Then the duration of the procedure can be importantly reduced. Reduction of time under anesthesia, and minimizing invasive procedures, are of great importance to the patient, and often are critical to his recovery.

Examples of the tissues subject to this invention are as follows. Tubular tissue: veins and arteries (blood vessels), fallopian tubes, vas deferens, ureters, urethras, limphatics, intestines, esophagus, and stomach. Linear tissue: muscles and nerves. These are given by way of example, and not of limitation, because there are others. These are all characterized by shape or cellular construction such that linear elongation is possible. This invention is not intended for expansion of skin, whose properties are quite different.

Another problem with existing procedure is the need to make two separate sutured butt-type joinders, each of which inherently requires surgical effort and subsequent problems.

Still another frequently-encountered problem is the incorporation into the vessel of a body having different physical or physiological properties at the abutting joinders. It is far preferable to unite ends of identical tissue, rather than to incorporate a structure having different properties. In many situations the joinder of two ends which were formerly part of a continuous vessel, and whose locations were spaced apart, cannot be accomplished merely by pulling the ends toward each other.

By way of further background, blood vessels will be given as an example. The other tissues described function similarly with this invention.

Blood vessels do have some elasticity which permits their length to be varied somewhat. However, these vessels are not simple structures. Instead they have at least several interior physiological layers as a lining which do not tolerate strong compressive or gripping forces. Such forces can result in bruises readily cause embollisms and clots. To grip a vessel strongly and stretch it risks severe damage to the vessel.

However, a blood vessel inherently has sufficient elasticity and yield within acceptable limits that an extension of perhaps up to 50% can be attained. Thus, if the remaining portions of the vessel can be permanently and sufficiently elongated to reconstruct the excised length, then the ends to be joined can be in a nearly relaxed state. Of course this assumes that the elongation did not harm the vessel, and especially its lining. This requires a gradual and gentle procedure which does not require a strong gripping force on the vessel, or any abrupt stretching force. These objectives cannot be attained with known techniques and instrumentation, but they can be attained by means of this invention.

When optimally used the device is expanded and relaxed at least three times, and fragments of the lining or whatever which may result from these forces can be washed out with the blood or whatever other fluid may be involved. Depending on circumstances, only one or two expansions may be needed. In any event, this device enables the tissue to be elongated without substantial trama.

While considering this invention, one should keep in mind that it is employed as part of a surgical procedure which almost always involves general anesthesia. It is well-established that morbidity of operations is strongly affected by the duration and depth of the required anesthesia. Furthermore, the surgeon is likelier to be fatigued by a procedure of longer duration than one of a shorter duration.

One significant example is the replacement of a portion of the length of a coronary artery with a length of a vein taken from the leg. The harvesting of the vein from the leg generally takes about 45 minutes to 1 hour. This is mostly because of the additional separate procedure to obtain the vein from the leg.

In contrast, when it can be employed, the procedure of this invention can render the vessel transplant unnecessary. Further, it can be accomplished in only about ten to fifteen minutes under acute operative conditions.

BRIEF DESCRIPTION OF THE INVENTION

This invention utilizes an expandable envelope one of whose dimensions increases with the expansion of the envelope. The envelope is placed immediately under the vessel, between supporting anatomy and the vessel, with the vessel aligned with that dimension. The envelope initially is uninflated and has a low volume. Then the envelope is gradually expanded by injection of a fluid into it. As it expands, the vessel's length along the envelope increases with the envelope's increase of length along that dimension.

Because blood vessels are generally restrained against substantial longitudinal movement by attachment to bone, muscle or other supportive anatomy, placing the envelope between the vessel and the supporting anatomy, enlargement of the envelope will be effective in elongating the vessel. The vessel will have been detached from the supporting anatomy at the region to be elongated, but it will remain attached beyond this separate area so a stretching action will occur between them, and will not merely result in a general pull on the entire length of the vessel, which could frustrate localized elongation. At the same time, the restraint on the "fixed" portions of the vessel will be those which it customarily has, and these are not pinching type grips. Thus, although grips could be provided to hold the vessel at each end of the envelope, they are not necessary.

It is not best practice to stretch the defective portion of the vessel, because this portion will be discarded, and elongation of it confers no benefit. Accordingly this procedure contemplates elongating a length of healthy tissue spaced from the defective segment. Then when the defective segment is removed, that end of the vessel which has been elongated will be pulled toward the resulting gap, and sutured directly to the other end of the incision.

The resulting vessel is not longitudinally stressed, and includes only one abutment joinder. The number of sutured joinders has been reduced by half, there is no discontinuity in the physical or physiological constitution of the repaired vessel. It has been done quickly.

As simple as it appears, there are latent difficulties which have had to be overcome. The device as used is not an implantation in the sense that the incision which enabled it to be placed is closed. It is not closed. Especially for smaller diameter vessels, the elongation process should take no more than about 10 to 15 minutes. Furthermore, it is not contemplated to attach the vessel to the envelope. Accordingly, there is a substantial potential for the stretched vessel to slide sidewardly off of the envelope.

Even more, the envelope rests upon supporting anatomy, and the entire field is wet and slippery, and is irrigated during the procedure. Downward pressure exerted by the stretched vessel on the top of the envelope could exert an eccentric force on the envelope which could cause it to skid to one side.

In either or both of said events, the envelope and vessel would not remain aligned so as to exert the stretching action. In the brief procedure in an open incision contemplated by the invention, such events will quickly be noticed. More importantly, the envelope itself is surfaced in such a way as to reduce the risk of either such event. It should be noted that efforts have been made to elongate vessels with the long-term use of expanding envelopes. These have actually been implanted and the incision has been closed. The problem is that failure of the assembly to maintain the proper alignment is not learned until the incision is again opened, and then the procedure is imperiled had there been a failure. To strap the tissue in place is to risk damaging the tissue. This invention avoids that risk.

Accordingly, the envelope according to this invention includes surface means on the envelope which encourage the vessel to stay in place on the envelope and not slip off, and for the envelope to remain in place relative to the supporting anatomy, and not to slide or roll out from beneath the vessel.

The above and other features of this invention will be fully understood from the following detailed description and the accompanying drawings, in which:

DETAILED DESCRIPTION OF THE INVENTION

Figure 1:
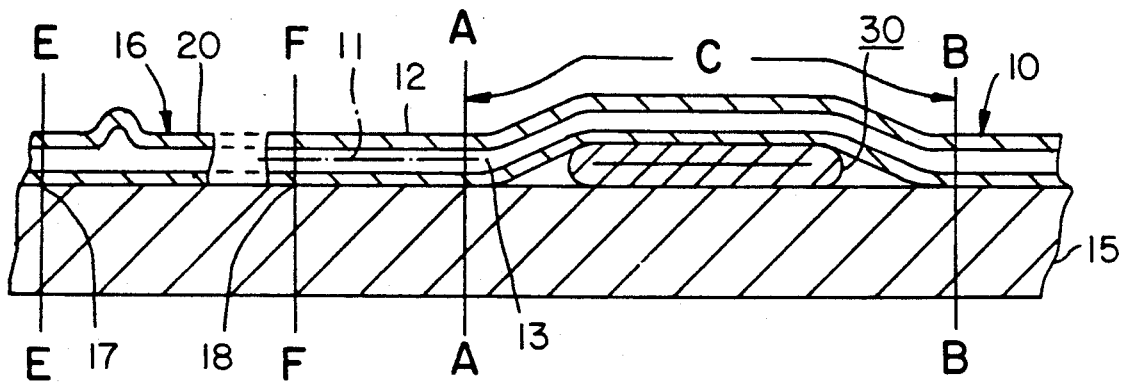
FIG. 1 is a longitudinal section showing the envelope deflated and placed to elongate tissue, in this case a blood vessel.
Figure 2:
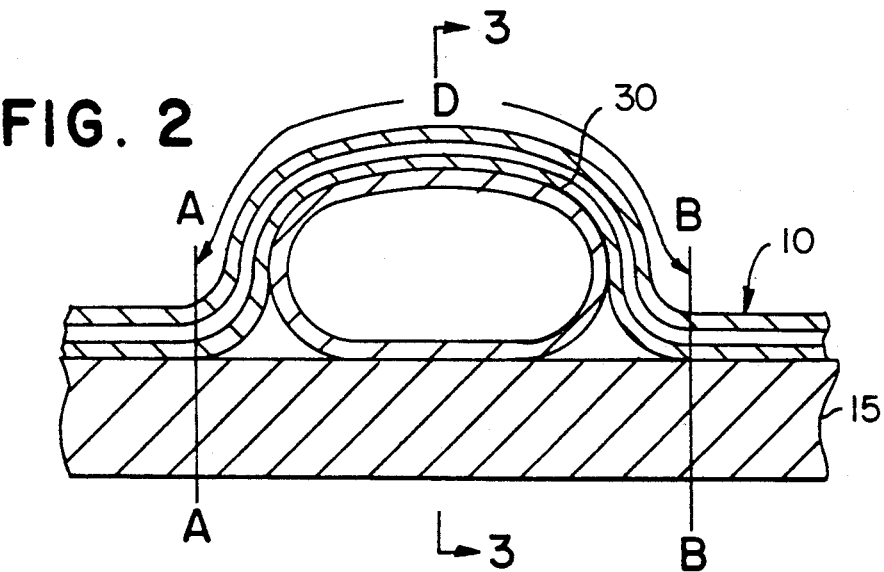
FIG. 2 is a view as FIG. 1, showing the envelope inflated and elongating the vessel.
Figure 3:
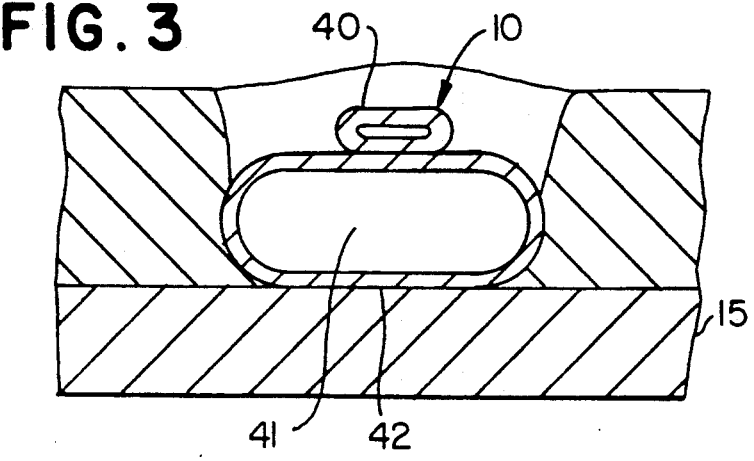
FIG. 3 is a cross-section taken at line 3—3 in FIG. 2.

In FIGS. 1-3, a blood vessel 10 having an axis 11 of elongation is shown. It is a tubular conduit having an external wall 12 and an internal lumen 13 through which the blood flows. In its initial unstressed condition (FIG. 1), it lays along an anatomic support or substrate 15 such as muscle or bone. This relationship is shown only schematically.

It is intended to elongate the length of the vessel between point A and point B. It is presumed that one of these points is not far distant from a defective segment 16 of the vessel, where it is to be removed or from a missing segment, perhaps as the consequence of a trauma. The defective segment is to be cut at planes E and F in FIG. 1, and ends 17, 18 of the vessel are to be abutted and joined. The objective is to replace by elongation the length between planes A and B, the vessel length which is excised between planes E and F.

The elongation occurs along the length of the segment to be elongated. Initially as shown in FIG. 1, the longitudinal length between planes A and B is denoted as C. In FIG. 2, after elongation, it is denoted as D. The difference in length between C and D is the elongation sought by this invention. It is intended to be at least as long as the distance between planes E and F, the segment 20 to be removed. After removal of segment 20, ends 17 and 18 are joined (or the other end of a damaged vessel).

In order to elongate segment A-B a deflated envelope 30 is initially placed between the anatomical support and the vessel, as shown in FIG. 1. The envelope is made of material having sufficient elasticity to expand as required without rupture. For service in the body, a medical grade silicon elastomer is preferred. This is a material commonly used in tissue expanders for expanding the skin. The envelope may have any desired dimensions in plan view. Because of the procedures required, it will usually have a limited width G (FIG. 4), and a length which nearly approximates the straight line distance between A and B.

Figure 4:
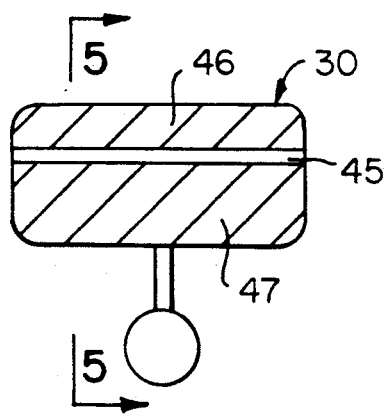
FIG. 4 is a top view of the envelope used in FIG. 1, deflated.

Whatever the initial shape may be, upon inflation the envelope tends toward the spherical—no planar surfaces will remain. The preferred shape is shown in FIG. 4. It is generally rectangular with a dimension of width 31 and a dimension of length 32 in the relaxed deflated condition.

Figure 9:
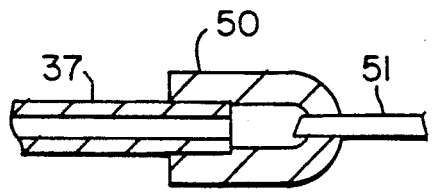
FIG. 9 is a fragmentary side view, partly in cross-section, showing an alternative to a reservoir.

The envelope has a wall 35 which defines an internal chamber 36. A fill tube 37 enters this chamber from a reservoir 38 as shown in FIGS. 1–7 or a valve as shown in FIG. 9. The reservoir is made of a material which seals against a needle track. The volume of a fluid injected into the reservoir will be equal to that which enters the envelope to enlarge it. The enlargement is therefore known. Also, fluid withdrawn from the reservoir can serve to deflate the envelope, as will be described below.

FIG. 9 shows an alternative to the reservoir. A valve 50 is provided as a self-sealing fill port. It is a self-sealing puncturable cap fitted over the end of the fill tube. It can be pierced by a syringe needle 51 through which fluid can be injected or removed. When the needle is withdrawn, its track closes, and in this sense the cap is a valve. Other valves or valve equivalents could also be used in place of the reservoir.

Figure 5:
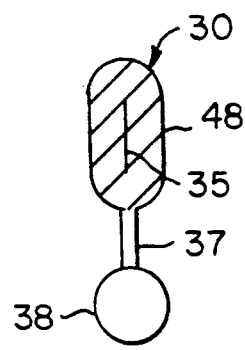
FIG. 5 is a side view of FIG. 4.
Figure 6:
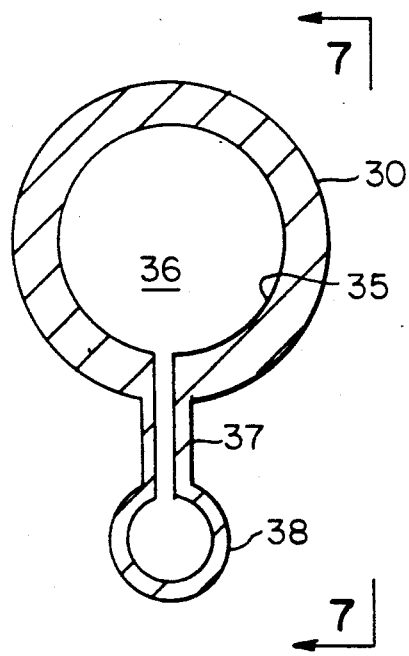
FIG. 6 is a cross-section showing the envelope of FIG. 4, inflated.
Figure 7:
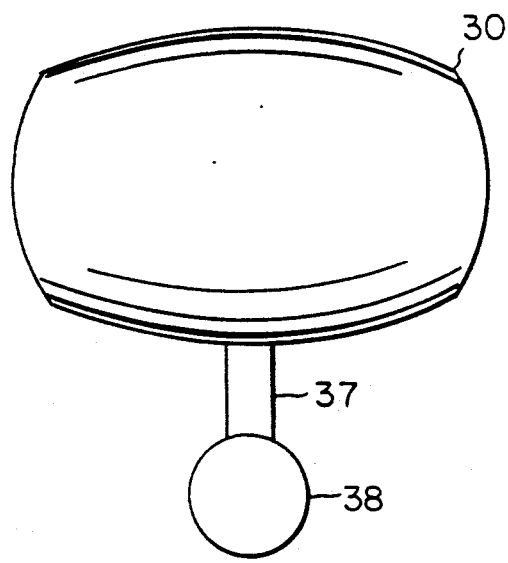
FIG. 7 is a side view of FIG. 6.

The envelope is preferably flat when deflated as shown in FIGS. 4 and 5, and enlarges as shown in FIGS. 2,3,6 and 7.

With reference to FIG. 3, it will be noted that the vessel has a nominal center 40, the envelope has a nominal center 41, and there is a center of contact 42 between the envelope and the anatomical support. When these stay aligned, the device functions optimally. But if the vessel slips to one side of a line drawn through centers 41 and 42, it will tend to slip off of the envelope and elongation will not occur.

Similarly, if the force exerted by the vessel on the envelope is off of the line, there could be a tendency of the envelope to slide to one side, and the vessel could slip off of the envelope.

Also, because the length of the elongated vessel differs from that of the envelope, it is best practice to permit the two to slip relative to one another along the line of elongation.

For the above reasons, a path 45 along the dimension of elongation is formed on the surface of the envelope which is smooth and offers no significant resistance to slippage of the vessel on it.

On each side 46, 47 of the top of the envelope, the surface is treated by surface means so as to be resistant to lateral slippage of the vessel. Raised studs along the edge of the path are one example. Preferably the sides will merely be roughened, perhaps by being formed in a die which has been sandblasted or peened.

Also, the bottom 48 of the envelope which contacts the anatomical support will be similarly treated. Thus, the three element system is stabilized, and the vessel will remain in place to be elongated.

Figure 8:
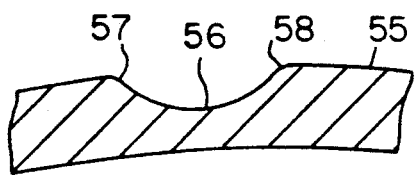
FIG. 8 is a fragmentary cross-section showing another embodiment of surface means to stabilize the vessel.

Another embodiment of surface means to restrain the vessel laterally is shown in FIG. 8. An envelope 55 in all other respects similar to those already described, has a groove 56 formed as the "path". The walls 57, 58 at each side of the recessed groove provide the restraint. Even when the groove is used, surface means at each side of it, and on the bottom, offer advantages.

In this procedure, it is best practice to exert elongation forces incrementally, with relaxation between each incremental exertion. This has two advantages. First it is better to release the elongation force periodically to enable blood to flow for a time sufficient to prevent necrosis.

Second, it appears that if the vessel is stretched beyond its elastic limit and then is relaxed, and then is again stretched beyond its elastic limit and relaxed, a greater permanent elongation with least trauma can be obtained.

These criterias also apply to the other tissues of interest in this invention. Again, elongation of blood vessels is described herein as a general example, and not as a limitation.

Generally about four expansions, each larger than its predecessor for about 1½ minutes each, with about ½ minute relaxation between them, can result in an elongation of about 50% of the initial length of most tissues of interest. When tubular tissue is being treated, it may be desirable to enable flow to be restored for a short period, and relaxation enables this.

The above procedure exemplifies the elongation of any tubular tissue. Similar procedures will be used for linear tissue, with similar results. Generally the tissue and the envelope will be irrigated further to assure axial freedom of the tissue on the envelope.

This procedure and its envelope are useful in acute operative circumstances, and do not contemplate longer-term implantation.

It should be understood that the shape of the envelope is arbitrary. It is the length of the respective chords C and D that is important to this invention.

This invention is not to be limited by the embodiments shown in the drawings and described in the description, which are given by way of example and not of limitation, but only in accordance with the scope of the appended claims.

We claim:

1. A procedure for elongating tubular or linear tissue to provide additional inherent length thereof thereby to enable a joinder with a severed end of the same tissue, said procedure comprising:

(a) placing a deflated inflatable envelope between said vessel and an adjacent anatomical support, with the tissue aligned with a dimension of the envelope which lengthens when the envelope is inflated;

(b) without closing the incision which gives access to said vessel, inflating the envelope to elongate the tissue, exceeding the elastic limit of said tissue, but not exceeding its yield point;

(c) following inflation of said envelope, deflation of said envelope, succeeded by another inflation of the envelope to elongate said tissue beyond a new elastic limit established after the previous elongation and deflation; and (d) deflating and removing said envelope, and drawing the severed ends of the tissue together to be joined.

2. An inflatable envelope for elongation of tubular or linear tissue, comprising: a closed fluid-impermeable envelope enclosing a chamber, said envelope being flexible and elastic, and having an outer surface with a dimension whose length increases when the envelope is inflated, the outer surface of the envelope having (a) a smooth path along said dimension which enables free sliding movement between the tissue and the path; (b) a surface modification on the side of the outer surface of the envelope facing away from the path that impedes sliding movement between the envelope and an anatomical support against which it is to bear; (c) means at each side of said path over which the tissue will not slide freely, whereby the tissue tends to remain aligned on said path; and (d) a fill tube making a fluid connection with said chamber to enable injection of fluid into the chamber and withdrawal of fluid from the chamber, to inflate and deflate the device.

3. An inflatable envelope according to claim 2 in which a puncturable reservoir is connected to the fill tube to enable fluid to be injected into and removed from the envelope, from the reservoir to and from the fill tube.

4. An inflatable envelope according to claim 2 in which a valve is fitted to said fill tube to enable fluid to be injected or removed.

5. An inflatable envelope according to claim 2 in which said path comprises a groove in said surface with a bottom and two side walls, said side wall comprising said means.

6. An inflatable envelope according to claim 2 in which said means comprises studs on said surface.

* * * * *